(12) United States Patent
Mermet

(10) Patent No.: US 9,919,113 B2
(45) Date of Patent: Mar. 20, 2018

(54) LUER LOCK ADAPTOR

(75) Inventor: Emeric Mermet, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 409 days.

(21) Appl. No.: 13/375,807

(22) PCT Filed: Jun. 3, 2009

(86) PCT No.: PCT/IB2009/006092
§ 371 (c)(1),
(2), (4) Date: Mar. 2, 2012

(87) PCT Pub. No.: WO2010/140019
PCT Pub. Date: Dec. 9, 2010

(65) Prior Publication Data
US 2012/0157928 A1 Jun. 21, 2012

(51) Int. Cl.
*A61M 5/34* (2006.01)
*A61M 39/10* (2006.01)
*A61M 5/31* (2006.01)

(52) U.S. Cl.
CPC ............ *A61M 5/345* (2013.01); *A61M 5/344* (2013.01); *A61M 39/10* (2013.01); *A61M 39/1011* (2013.01); *A61M 5/3134* (2013.01); *A61M 5/347* (2013.01); *A61M 2005/3104* (2013.01); *A61M 2039/1077* (2013.01); *Y10T 29/49826* (2015.01); *Y10T 156/10* (2015.01)

(58) Field of Classification Search
CPC .... A61M 5/3134; A61M 5/344; A61M 5/345; A61M 5/347; A61M 2005/3142; A61M 2005/341; A61M 5/346; A61M 5/348; A61M 5/349; A61M 39/10; A61M 39/1011; A61M 2039/1077
USPC ................................ 604/240, 241, 242, 243
See application file for complete search history.

(56) References Cited

U.S. PATENT DOCUMENTS

| 1,727,755 | A | * | 9/1929 | Dickinson | B21D 49/00 174/188 |
| 4,084,588 | A | * | 4/1978 | Koenig | A61M 5/34 604/205 |
| 5,624,402 | A | | 4/1997 | Imbert | |

(Continued)

FOREIGN PATENT DOCUMENTS

| DE | 3515665 C1 | 5/1986 |
| EP | 0098411 A2 | 1/1984 |

(Continued)

*Primary Examiner* — Shefali Patel
(74) *Attorney, Agent, or Firm* — The Webb Law Firm

(57) ABSTRACT

An adaptor for connecting a second connector to a drug delivery device includes at least a container for a product, the container including a distal tip and an axial passageway defined through the distal tip, the adaptor having a longitudinal axis and being intended to be mounted on the distal tip, the adaptor including a first part and a second part, the first part being provided with an unreleasable attachment able to fix the first part to the distal tip, the second part being provided with a connector able to connect the second part to the second connector, the adaptor further including a securer able to anchor the first part to the second part. The drug delivery device includes the adaptor and a method for mounting the adaptor.

24 Claims, 4 Drawing Sheets

(56) References Cited

U.S. PATENT DOCUMENTS

| | | | |
|---|---|---|---|
| 6,520,935 B1 * | 2/2003 | Jansen | A61M 5/3134 604/111 |
| 7,648,481 B2 | 1/2010 | Geiger et al. | |
| 2003/0163093 A1 | 8/2003 | Thibault et al. | |
| 2011/0130717 A1 | 6/2011 | David et al. | |

FOREIGN PATENT DOCUMENTS

| | | |
|---|---|---|
| EP | 0633038 A1 | 1/1995 |
| EP | 1600190 A1 | 11/2005 |
| GB | 2379253 A | 3/2003 |
| JP | 2005-296135 | 10/2005 |
| WO | 2006087763 A1 | 8/2006 |
| WO | 2008153019 A1 | 12/2008 |
| WO | 2009144583 A1 | 12/2009 |

\* cited by examiner

LUER LOCK ADAPTOR

CROSS REFERENCE TO RELATED APPLICATIONS

This application claims the benefit of priority to International Application No. PCT/IB2009/006092 filed on Jun. 3, 2009, the contents of which are hereby incorporated by reference in their entirety.

BACKGROUND

1. Field of the Invention

The present invention relates to an improved Luer lock adaptor for use with a drug delivery device. The adaptor allows a safe connection between the drug delivery device and a connector to be coupled to the drug delivery device. The invention also relates to a drug delivery device provided with such an improved adaptor and to a method for mounting said adaptor on such a drug delivery device.

2. Description of Related Art

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Various medical devices are known for transferring and/or storing medical fluids, such as syringes, needle assemblies, perfusion devices, transfusion devices and connectors such as for example IV (Intra Venous), IM (Intra Muscular), subcutaneous connectors. It is essential for safety reasons that these various medical devices can be assembled together correctly and securely. The use of specific adaptors between the various medical devices makes it possible to assemble them, ensure a sealed connection and provide protection against the contamination of the medical liquid products they contain.

A conventional drug delivery device usually comprises a hollow body forming a container for a medical product: the distal end of the body forming the container usually comprises a tip in which an axial passageway is arranged and through which the said product is ejected from the container.

Usually, the adaptors are first mounted on the distal tip of the drug delivery device by friction force and the connector is then mounted on the free end of the adaptor, for example by screwing.

U.S. Pat. No. 5,624,402 describes such an adaptor of the prior art assembled on a distal tip of a drug delivery device. FIG. 1 of the present application shows a cross section view of such an assembling of the prior art. On FIG. 1, the container 101 of a drug delivery device 200 is provided with a distal tip 202 having an axial passageway 203. The container 201 is further provided with a stopper (not shown) enabling to push the medical product outside of the drug delivery device 200. An adaptor 205 is mounted on the distal tip 202. This adaptor 205 is provided with an annular ridge 206, radially expandable upon forces exerted on its inner wall and enabling the adaptor 205 to be friction forced on the distal tip 202 of the drug delivery device 200. Thanks to its capability to deform, the annular ridge 205 expands when it is friction forced on the distal tip 202 of the drug delivery device 200, until it gets stuck. The adaptor 205 is then supposed to be immobile with respect to the drug delivery device 200 thanks to friction forces present between the annular ridge 206 and the distal tip 202 of the drug delivery device 200. On its side opposite to the annular ridge 206, the adaptor 205 comprises internal threads 207 enabling threaded engagement of the adaptor 205 with a corresponding threaded structure 208 provided on a tip cap 209 or on a connector (not shown) to be assembled to the drug delivery device 200. The tip cap 209 is closed by an inner cap 210. The tightness of the assembling of the adaptor 205 on the drug delivery device 200 is ensured by the elastic deformation 211 of the inner cap 210 in the axial passageway 203 of the distal tip 202.

A problem encountered with such an adaptor 205 of the prior art is that the strength of the assembling of the adaptor 205 on the distal tip 202 depends firstly on the accuracy of the dimensions of the conical external surface of the distal tip 202 and of the adaptor 205, secondly on the force used to engage the adaptor 205 on the distal tip 202. Due to industrial tolerances, the conical assembling of the adaptor 205 on the distal tip 202 is therefore rather inaccurate and the strength of the assembling cannot be guaranteed.

There is therefore a need for an improved adaptor enabling to ensure a reliable assembling of the adaptor on a drug delivery device. There is also a need of a drug delivery device provided with such adaptor.

Medical uses require specific assembling conditions to ensure that the drug delivery device is not contaminated. A suitable quality level is obtained by performing the assembling in clean rooms in which the drug delivery devices are washed and siliconized to allow a better gliding of the stopper. The friction force connection of such adaptor 105 on distal tip 102 of a drug delivery device 100 is highly impacted by the silicon that may inadvertently be applied on the outside surface of the distal tip 102.

There is therefore a need for an improved adaptor enabling a reliable assembling on the distal tip of a drug injection device. There is also a need of a drug delivery device provided with such adaptor.

Other problems have been reported concerning the use of adaptors with various drug delivery devices. Indeed, most of the adaptors that are available for use in the medical field for the purpose of connecting drug delivery devices with connectors are made of plastic material. The capability of deformation of such plastic material is influenced by aging and temperature conditions. In addition, plastic materials are sensitive to sterilization process.

As a primary result the range of available plastic material usable in the medical field is limited in term of composition and of color.

As a secondary result, it may happen that, for example after a certain time or after having been submitted to specific conditions like sterilization temperatures, elastic characteristics of the plastic material chosen are damaged. In consequence, the adaptor does not remain immobile with respect to the distal tip of the drug delivery device. In particular, it may happen that the friction forces are not important enough to prevent the adaptor from rotating, particularly when the user tries to screw a connector on to the adaptor. It is therefore impossible for the user to determine whether the connector is well fitted in the adaptor or not and, as a consequence, whether the connector is well connected to the distal tip of the drug delivery device. An incorrect connection between the drug delivery device and the connector may cause the displacement of the adaptor and/or of the connector in regards to the drug delivery device, that could lead to leaks of product and therefore incorrect doses administered to the patient and product waste. To overcome this problem and ensure good connection between the connector and the adaptor, when screwing the connector on the adaptor, the users tend to hold the drug delivery device by the adaptor itself. The adaptor having a small size, it is difficult to handle it efficiently. During this operation, the fingers of the user are close to the tip of the injection drug delivery device and to the axial passageway, increasing the risk of contamination of the medical liquid contained.

There is therefore a need for an improved adaptor enabling the use of a wider range of material while ensuring an efficient and reliable connection between the drug injection device and the connector. There is also a need of a drug delivery device provided with such adaptor.

In order to guaranty a friction force high enough to ensure the correct connection between the drug delivery device and the adaptor, the diameters of both the injection device tip and the adaptor are tightly adjusted. Due to these tight dimensions, the assembling of the adaptor on the injection device requires a high force that often generates high stress in the glass tip. This stress may create cracks that render the drug delivery device not usable.

There is therefore a need for an improved adaptor enabling to avoid damaging the distal tip of the injection device on which it is assembled. There is also a need for an improved adaptor enabling a wider range of technologies to fix the adaptor on the tip of the drug delivery device. There is also a need of a drug delivery device provided with such adaptor.

There is also a need for an adaptor allowing a reproducible connection of a connector to a drug delivery device so that the desired position of the connector with respect to said drug delivery device is attained and then secured, regardless of which conditions (temperature, pressure, aging, etc. . . . ) the adaptor or part of the adaptor has been submitted to during its manufacture and/or its mounting on the delivery device.

SUMMARY

One aspect of the present invention is an adaptor for a drug delivery device comprising at least a container for a product, said container comprising a distal tip and an axial passageway defined through said distal tip, said adaptor having a longitudinal axis A and being intended to be mounted on said distal tip, characterized in that said adaptor includes at least a first part and a second part, said first part being provided with attaching means able to attach said first part to said distal tip, said second part being provided with connecting means able to connect said second part to a connector, said adaptor further includes securing means for securing said first part to said second part.

The adaptor of the invention may be used in particular for connecting a connector to a drug delivery device. As will appear from the description below, such an embodiment of the adaptor allows differentiation of the securing function from the attaching function. The first part is ensuring the attaching function and the second part is ensuring the securing function. Therefore, on one hand, the first part can be specifically designed and made of a most suitable material to provide the best attachment on the injection device. The possibilities that the adaptor of the invention be displaced and eventually misplaced on the distal tip of the drug delivery device it is intended to be mounted onto are therefore greatly limited. The adaptor of the invention therefore allows a reproducible connection of a connector and ensures that the connector is correctly positioned with respect to the drug delivery device. On the other hand, the second part can also be specifically designed and made of a most suitable material to provide the best securing of the connector on the first part and therefore on the injection device. The material used for the second part does not need to answer to the attaching function ensured by the first part. Therefore, the second part can be made of a material chosen in a wider range of materials.

In an embodiment of the invention, said first part having an annular shape and being sized and shaped to receive said distal tip, the attaching means include at least one attaching surface located on an inner surface of said first part. The attaching surface may be provided with a rough surface.

In an embodiment of the invention, at least one of said first part and second part is provided with at least one anchoring abutment, the other one of said second part and first part is provided with at least one anchoring hook, one of said anchoring abutment and said anchoring hook being elastically deformable to allow its engagement respectively with said anchoring hook or said anchoring abutment, said anchoring hook and said anchoring abutment being arranged to prevent, when engaged with each other, the longitudinal displacement of said first part and said second part apart from each other, said anchoring abutment and said anchoring hook forming at least part of said securing means.

In an embodiment, said adaptor is provided with an access area able to allow the access to said elastically deformable anchoring hook or anchoring abutment by a user when said first part and said second part are secured to each other, in order to elastically deform said elastically deformable anchoring hook or said anchoring abutment and release said securing means.

In an embodiment, the adaptor is provided with said first part and said second part separate from each other. In another embodiment, the adaptor is provided with said first part and said second part secured to each other.

In an embodiment of the invention, the adaptor further comprises positioning means provided partly on said first part and partly on said second part and able to prevent, when said first part and said second part are secured to each other, the angular displacement of said first part in regards to said second part.

In an embodiment of the invention, at least one of said first part and said second part is provided with at least one positioning peg, the other one of said second part and said first part being provided with at least one positioning hole arranged to receive said positioning peg when said first part and said second part are secured to each other, said positioning hole and said positioning peg forming at least part of said positioning means.

The second part may be provided with at least one thread forming at least partially said connecting means.

In an embodiment, the second part is provided with closing means intended to close a distal end of said second part, said closing means being engaged with said connecting means.

In an embodiment of the invention, said second part has an annular shape with at least one traversing hole defined therethrough along said longitudinal axis A.

The first part and second part may be made of different material. For example, the first part may be made of a material selected in the group comprising polycarbonate, polyoxymethylen (POM) and combinations thereof. The integrity and properties of a first part made of such a material are not damaged when said first part is submitted to specific temperature and pressure conditions, such as those needed for a washing, sterilization or siliconization process for example. For example, the second part may be made of a material selected in the group comprising polystyrene shock, polypropylene and combinations thereof. In embodiments, the second part may be made of any other suitable material that can be cheaper than the material used for the first part, more widely available and accepting aesthetical modifications such as a colorant addition to ease the product identification.

The first and second parts may have different colors: this allows to set up a code for the user to categorize the adaptor depending on which drug delivery device it is intended to be used with.

Another aspect of the present invention is a drug delivery device comprising at least a container for a product, said container comprising a distal tip and an axial passageway defined through said distal tip, characterized in that it further comprises at least one adaptor as previously described.

In an embodiment of the invention, at least said first part of said adaptor is mounted on said distal tip, said first part being fixed to said distal tip by unreleasable fixing means. The unreleasable fixing means may be chosen in the group comprising gluing, fretting, binding, melting and combinations thereof.

In an embodiment of the invention, said second part of said adaptor is secured to said first part, said securing means securing said first part to said second part.

The container may be made of glass.

Another aspect of the present invention is a method for mounting an adaptor as previously described onto a drug delivery device comprising at least a container for a product, said container comprising a distal tip and an axial passageway defined through said distal tip, said method comprising at least the following steps:
  providing the adaptor comprising a first part and second part separate from each other,
  mounting said first part of said adaptor on said distal tip by fixing said first part to said distal tip with unreleasable fixing means,
  engaging said second part of said adaptor with said first part and securing it to said first part by means of said securing means.

In an embodiment of the invention, said adaptor being provided in the first place with its first part and second part secured to each other by means of said securing means,
  said securing means are disengaged in order to detach said first part and said second part from each other, so as to provide said adaptor with its first part and second part separate from each other.

In an embodiment, said unreleasable fixing means are chosen in the group comprising gluing, fretting, binding, melting and combinations thereof.

Another aspect of the present invention is a method for mounting an adaptor as previously described onto a drug delivery device comprising at least a container for a product, said container comprising a distal tip and an axial passageway defined through said distal tip, said method comprising at least the following steps:
  said adaptor is provided with its first part and second part secured to each other by means of said securing means,
  said securing means are disengaged in order to detach said first part and said second part from each other, said first part of said adaptor is mounted on said distal tip by fixing said first part to said distal tip by unreleasable fixing means,
  said second part of said adaptor is engaged with said first part and secured to said first part by means of said securing means.

BRIEF DESCRIPTION OF THE DRAWINGS

The invention and the advantages that arise therefrom will clearly emerge from the detailed description that is given below with reference to the appended drawings in which.

DETAILED DESCRIPTION OF PREFERRED EMBODIMENTS

Figure 1:
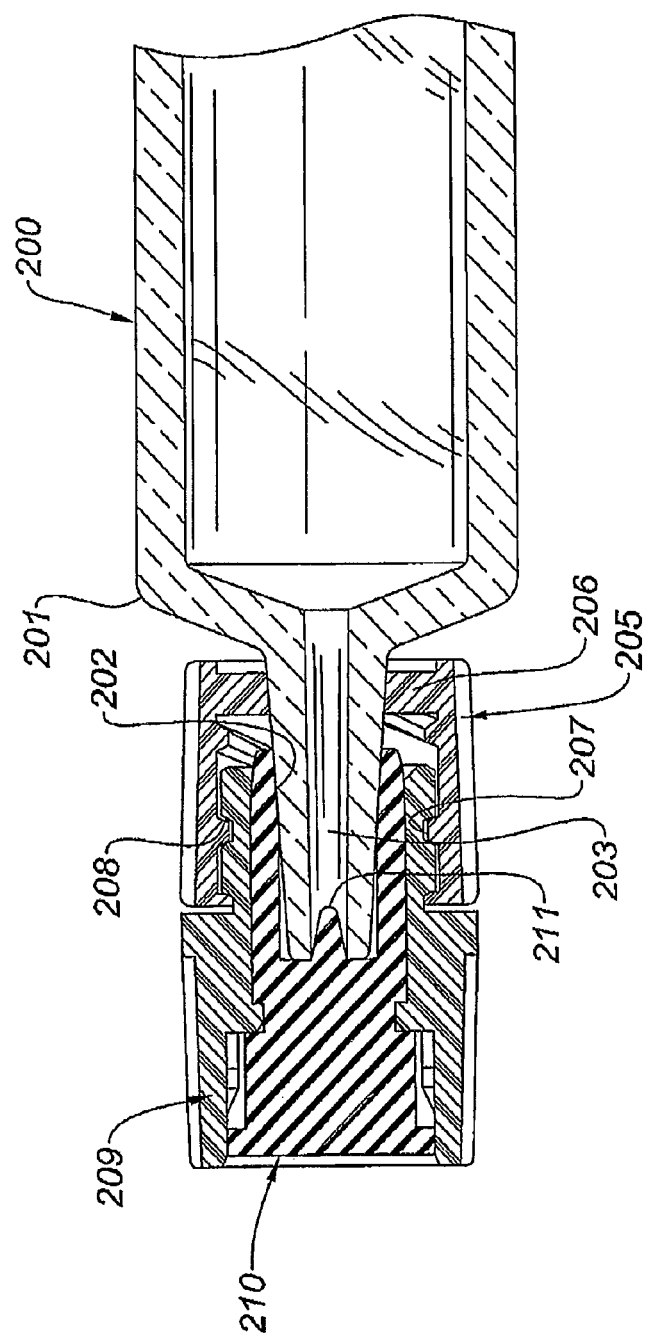
FIG. 1 is a cross section view of an adaptor of the prior art, the adaptor being mounted by friction on the distal tip of a drug delivery device.
Figure 2:
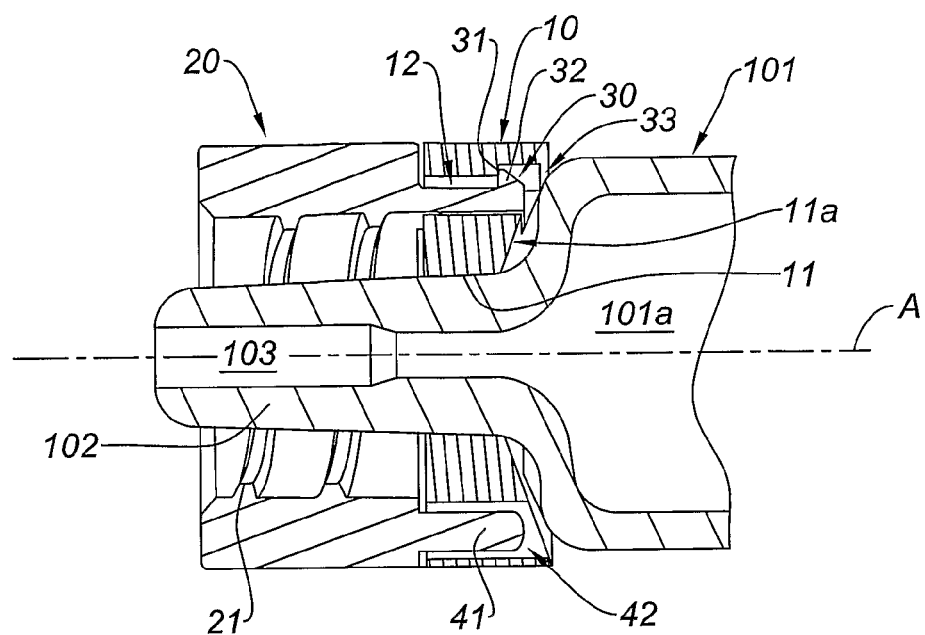
FIG. 2 is a cross section view of an adaptor of the invention, the adaptor being mounted on the distal tip of a drug delivery device according to the method of the invention.
Figure 3:
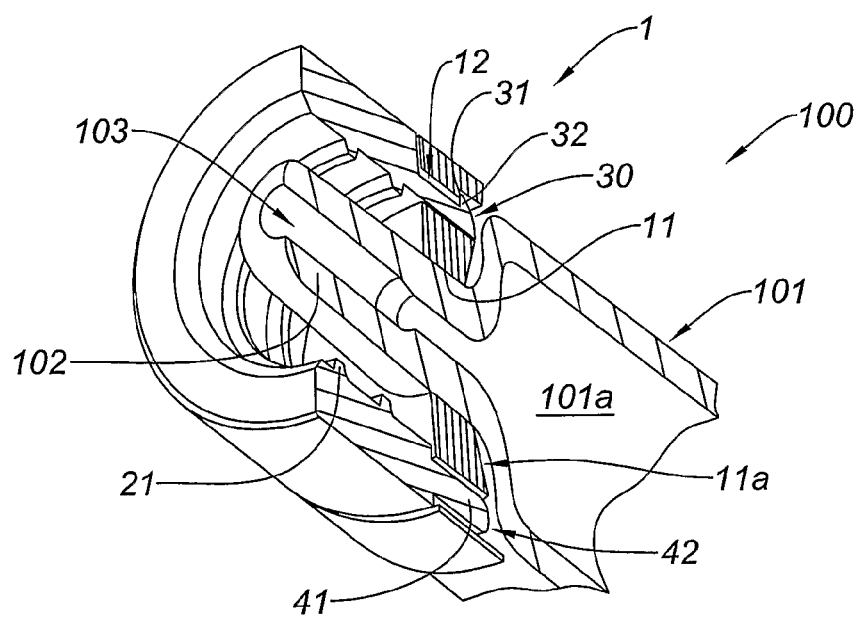
FIG. 3 is a perspective cross section view of the adaptor of FIG. 2, FIGS. 4A and 4B are perspective view of the adaptor and the drug delivery device of FIG. 2 before or during assembling.

With reference to FIGS. 2 and 3 is shown an adaptor 1 according to the invention, the adaptor 1 being mounted on a drug delivery device 100 according to the method of the invention.

The drug delivery device 100 of the invention shown on FIG. 2 comprises a container 101 having a distal tip 102 with a longitudinal axis A. On the example shown, the container 101 and the distal tip 102 are made of one single element made of glass. The container 101 has a tubular shape and defines a reservoir 101a for a product, for example a medical fluid. The container 101 and the distal tip 102 are preferably made of glass material. In another embodiment not shown, the distal tip 102 could be under the shape of an additional element provided on the extremity of the container 101.

The container 101 may be sealed at its proximal end by a piston (not shown). The distal tip 102 encompasses an axial passageway 103 aligned with the longitudinal axis A for the transfer of the product, either from the container 101 to a connector (not shown) such as for example an IV (Intra Venous) connector, an IM (Intra Muscular) connector, a subcutaneous connector, or others, or from such a connector to the container 101.

The adaptor 1 comprises a first part 10 and a second part 20. In the example shown, the first part and the second part have annular shapes and are sized and shaped so as to receive the distal tip 102: on the example shown, they have globally the shape of circular rings (10, 20).

Figure 4A:
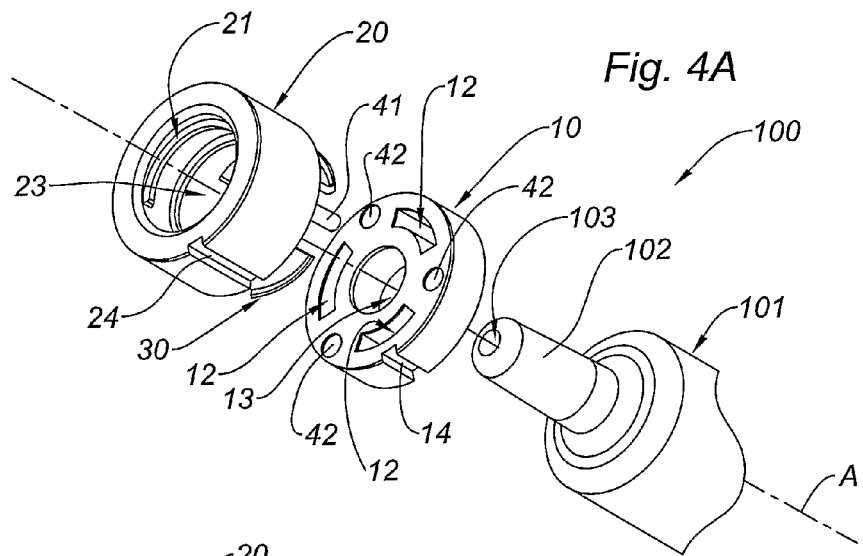
Figure 4B:
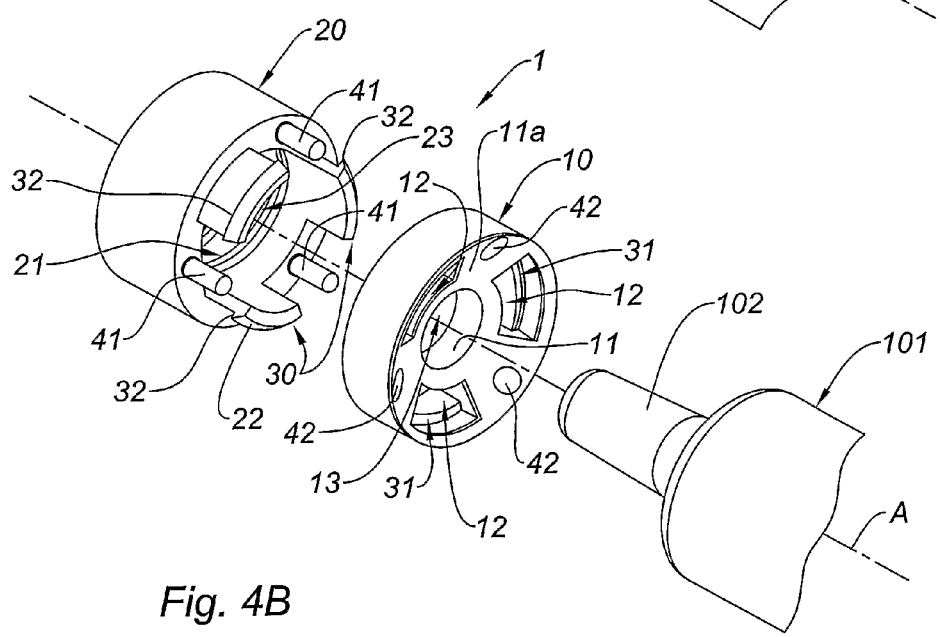

With reference to FIGS. 4A and 4B, the first part 10 is provided with three circular traversing positioning holes 42, angularly regularly distributed around the longitudinal axis A, the function of which will be explain after. In another embodiment not shown, the first part is provided with positioning holes emerging from the distal face of the first part but that are not traversing said first part.

Still with reference to FIGS. 4A and 4B, the first part 10 is also provided with three traversing anchoring holes 12 angularly regularly distributed around the longitudinal axis A, the function of which will be explain after. Each anchoring hole 12 has a shape of an arc of circle oriented toward the longitudinal axis A. The anchoring holes 12 are provided, toward their proximal end, with a wider space forming an anchoring abutment 31 (see FIGS. 4A and 4B), used as described after, to anchor the second part 20 onto the first part 10.

On the example shown, the first part, under the form of a ring 10, is further provided with a traversing first engagement hole 13, shown on FIGS. 4A and 4B, coaxial with the longitudinal axis A and defining an attaching surface 11, located on an inner surface of said ring 10 and oriented toward said longitudinal axis A. The attaching surface 11 is adjacent to an inclined complementary attaching surface 11a having a shape complementary to the one of the attaching surface 11 and forming part of the distal face of the first part 10. As described after, this attaching surface 11 and/or the complementary attaching surface 11a is able to be attached to the distal tip 102 of the container 101 and fixed thereof by unreleasable fixing means such as for example gluing, fretting, binding, melting. The attaching surface 11 and/or the complementary attaching surface 11a form attaching means which may contribute, in combination with said unreleasable fixing means, to ensure a reliable and durable attachment of the first part 10 on the distal tip 102 of the drug delivery device 100. By "unreleasable fixing means" it is to be understood that the first part 10 can not be disassembled from the distal tip 102 without breaking or damaging at least one of the first part 10 and/or the distal tip 102. These <<unreleasable fixing means>> are opposed to friction force means that could allow disassembling without damaging any of the part such as described in the prior art.

The attaching surface 11 and/or complementary attaching surface 11a can be provided with a rough surface for example partially coated with a roughening agent such as for example ceramic particles or obtained by grinding or any other suitable means. On the example shown, the attaching surface 11 is provided with a rough surface.

Still with reference to FIG. 4B, the second part 20 is provided with three positioning pegs 41, angularly regularly distributed around the longitudinal axis A. The positioning pegs 41, the function of which will be explain after, have shape and dimensions enabling their engagement in the positioning holes 42 of the first part 10.

The second part 20 is also provided with three anchoring hooks 30 angularly regularly distributed around the longitudinal axis A. The anchoring hooks 30, the function of which will be explain after, have the shape of an arc of circle and dimensions enabling their engagement in the anchoring holes 12 of the first part 10. Each anchoring hook 30 is provided with a nose 32 able to cooperate with the anchoring abutment 31 when the first and second part 10, 20 are engaged with each other. The anchoring hooks 30 are provided with an inclined distal surface 22 and are elastically deformable to allow their deformation and their engagement in the anchoring holes 12. As will appear later, the anchoring hooks 30 and the anchoring abutment 31 form securing means for securing the first part 10 to the second part 20.

The second part 20 is further provided with a traversing second engagement hole 23, shown on FIGS. 4A and 4B, coaxial with the longitudinal axis A and intended to receive the extremity of the distal tip 102 of the drug injection device 100. The second part, which on the example shown is under the form of a ring 20, is also provided with one thread 21, located on the inner surface of said ring 20, intended to cooperate with the thread of a connector (not shown) at the time of screwing the connector on the adaptor 1. Therefore, the connector (not shown), such as an IV connector, can then be screwed on the adaptor 1, in order to connect safely the drug delivery device 100 to the said connector so as to realize the transfer of the product from the drug delivery device 100 to the connector or vice-versa.

In the example shown, both the first and second parts (10, 20) are respectively provided, on their outer surface, with a first and a second longitudinal grooves (14, 24) shown on FIG. 4A. These first and second longitudinal grooves (14, 24) can be used to radially position the second part 20 in regards to the first part 10 during the assembling of the second part 20 on the first part 10, as will be described below.

In another embodiment of the invention not shown, the first part and the second part of the adaptor are provided with more or less positioning pegs and positioning holes and/or more or less anchoring abutments and anchoring hooks. The shape of the positioning means and securing means may also be chosen different from what is shown on the drawings.

In again another embodiment not shown, one or more of the positioning peg and/or positioning hole and/or anchoring hook and/or anchoring abutment can have a shape and/or dimensions different from the other positioning peg, positioning hole, anchoring hook and/or anchoring abutment. This specific shape and/or dimension may be used has a way to allow only one specific angular assembling position for the assembling of the second part on the first part. Such a specific angular position may be required for specific application.

Figure 5:
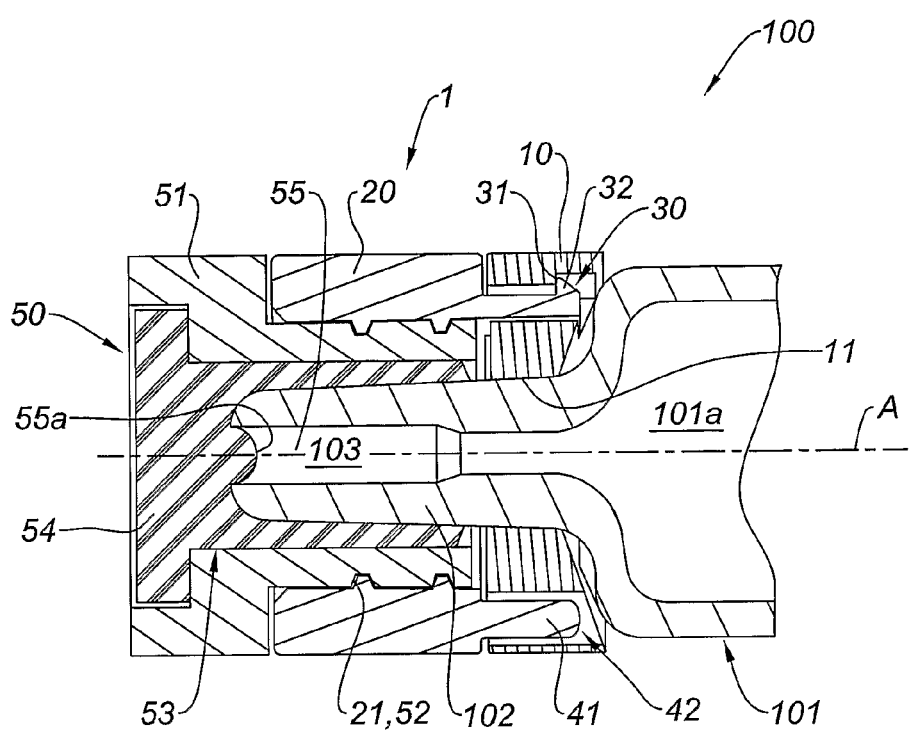
FIG. 5 is a cross section view of the improved adaptor and drug delivery device of FIG. 2 provided with a tip cap.

On FIG. 5 is shown the assembly of an injection device 100 provided with an adaptor 1, the distal end of which is closed by closing means 50. In this example the closing means are formed by a cap 50 screwed on the adaptor 1. The cap 50 is made of two parts, an outer part 51 and an inner part 54. The outer part 51 is provided with internal thread 52 intended to cooperate with the external thread 21 of the adaptor 1. The outer part 51 is also provided with an inner cylindrical opening 53 able to receive the inner part 54. The inner part 54 has globally a cylindrical shape and is provided with a longitudinal recess 55 provided with a distal wall 55a. The inner part 54 is generally made in a flexible material to allow the inner part 54 to firstly enable to ensure a tightly contact between the outer part 51 and the inner part 54 when assembled together and secondly allow the inner part 54 to deform itself around the extremity of the distal tip 102 and ensures the tight closing of the container 101. As shown on this figure, when the cap 50 is fitted on the adaptor 1, the distal wall 55a is resiliently deformed around the distal tip 102 of the drug delivery device 100 and ensures the tightness of the assembly. Therefore, no product can inadvertently leak out of the container 101.

The operation of mounting and fitting an adaptor 1 of the invention on a drug delivery device 100 of the invention in view of further safely connecting a connector on said drug delivery device 100 will now be described with reference to FIGS. 4A and 4B. In the example shown, the adaptor 1 is provided with the first part 10 and the second part 20 separate from each other. This allows in a first step to assemble the first part 10 on the distal end 102 of the drug delivery device 100 independently from the second part 20. Therefore, the first part 10 can be exposed to assembling specific conditions in term of pressure, temperature, humidity without impacting the second part 20. To better fulfill these specific conditions the first part is preferably made of polycarbonate, polyoxymethylen (POM) or combinations thereof. As the second part 20 will not be impacted by these specific conditions, the material of which the second part 20 is made of can be more widely selected in term of composition and/or color. It is therefore possible to choose a colored material for the second part, the color facilitating for example the identification of the product contained in the drug delivery device 100. The second part 20 is for example made of polystyrene shock, polypropylene or combinations thereof.

To perform the first step to assemble the first part 10 to the second part 20, the user engages the first part 10 on the distal tip 102 of the drug delivery device 100. The first part 10 can be stuck on the distal tip 102 by an unreleasable means such as glue previously applied on one or both of the first part 10 and distal tip 102. The glue can also be applied after the engagement of the first part 10 on the distal tip 102. The first part 10 can be fixed onto the distal tip 102 by any other suitable unreleasable fixing means such as fretting, binding, melting and combinations thereof. In particular, and on the example shown, the first part 10 is fixed to the distal tip 102 by means of its attaching means, ie the attaching surface 11, being glued onto the outer surface of the distal tip 102. After assembling, the drug delivery device 100, provided with the first part 10 fixed on said distal tip 102 with said unreleasable fixing means, can be washed and/or sterilized without any effect on the second part 20 not yet assembled, and without any risk that the first part 10 be displaced and/or misplaced with respect to said distal tip 102. The assembly of the drug delivery device 100 and the first part 10 can also be siliconized without any impact on the strength of the assembly, ie without any risk that the first part 10 be displaced and/or misplaced with respect to said distal tip 102.

In a second step, to assemble the second part 20 of the adaptor 1 to the drug delivery device 100, the user holds the drug delivery device 100 on which said first part is now fixed, and engages the second part 20 on the first part 10, by moving the drug delivery device 100 toward the second part 20 along the longitudinal axis A. As the user holds the drug delivery device 100 and not the first part 10, this prevents any contamination of the first part 10, particularly if in the first step the drug delivery device 100 and the assembled first part 10 have been washed. When the first part 10 and the second part 20 are engaged with each other, as shown on the FIGS. 2, 3 and 5, the three anchoring hooks 30 are positioned in the three traversing anchoring holes 12 of the first part 10. When moving the first part 10 toward the second part 20, the inclined surface 22 of the anchoring hooks 30 abut against the distal face of the first part 10. The anchoring hooks 30 are elastically deformed and engaged in the anchoring holes 12. Once the anchoring hooks 30 are fully engaged in the anchoring holes 12, the noses 32 of the anchoring hooks 30 are positioned in the wider space of the anchoring holes 12, allowing the anchoring hooks 30 to come back to their rest position and have their noses 32 to abut against the anchoring abutment 31. The anchoring of the second part 20 on the first part 10 is strong and this, even if the assembly of the drug delivery device 100 and the first part 10 was previously siliconized. Indeed, the anchoring holes 12 and anchoring hooks 30 ensure a strong physical anchoring. In this anchoring position, ie when the first part 10 and the second part 20 are secured to each other as just described, the longitudinal displacement of the first part 10 in regards to the second part 20 is then prevented by the anchoring hooks 30 and the anchoring abutment 31 forming reliable securing means for the adaptor 1. Each of the three positioning pegs 41 of the second part 20 is positioned in one of the three circular traversing positioning holes 42 of the first part 10. It appears clearly that the positioning pegs 41 and the positioning holes 42 are then preventing any angular displacement of the first part 10 in regards to the second part 20 and form reliable positioning means for the adaptor 1.

The anchoring hooks 30 and the anchoring abutment 31 therefore form securing means of the first part 10 to the second part 20. The positioning holes 42 and the positioning pegs 41 form positioning means provided partly on said first part 10 and partly on said second part 20 and able to prevent, when said first part 10 and said second part 20 are anchored to each other, the angular displacement of said first part 10 in regards to said second part 20.

As a consequence, when the user wishes to proceed to the further step of connecting to the adaptor 1 a connector, such as an IV connector, he just has to grasp the drug delivery device 100 in one hand and then to screw the connector on to the internal thread 21 of the adaptor 1 without fearing that the adaptor 1 may detach from the distal tip 102. The attaching function is ensured by the unreleasable fixing means and the attaching means 11 provided between the first part 10 and the drug delivery device 100. The securing function is ensured by the securing means provided between the first part 10 and the second part 20. When the external thread of the connector (not shown) is firmly screwed on the internal thread 21 of the adaptor 1, then the user knows that the drug delivery device 100 and the connector are tightly connected without any risk of leakage of the product to be transferred from the container 101 to the connector or vice versa. In case the injection device is provided with closure means such as shown on FIG. 5, before connecting the drug delivery device 100 fitted with the adaptor 1 with the connector, the user unscrews the cap 50 before screwing the connector on the adaptor 1.

The adaptor 1 is therefore securely prevented from rotating or translating with respect to the distal tip 103 around the longitudinal axis A, even after aging or after having been submitted to high temperatures such as sterilization temperature. The attaching means of the first part 10 on the distal tip 102 allows connecting safely a drug delivery device 100 to a connector without having to fear the adaptor 1 may detach from the drug delivery device 100 even in the case of use of high viscosity drug. The adaptor 1 of the invention renders the connection of a drug delivery device 100 to a connector, such as an IV connector, particularly simple, safe and reproducible.

The adaptor may also be provided with the first part 10 and the second part 20 engaged/secured with each other. In this case, it is preferable to disengage the first and second part 10, 20 from each other before fixing the first part 10 on the distal tip 102 and then anchoring the second part 20 on the first part 10 as previously described. Before the assembling of the adaptor 1 with the drug delivery device 100, the user can have access to the extremity of the anchoring hooks 30 through a free proximal access 33 provided in the proximal face of the first part 10 to disengage the second part 20 from the first part 10. This proximal access 33 is shown on FIG. 2 in a position where it is not usable anymore because of the drug delivery device 100 on which the adaptor is now fixed to. Before assembling the adaptor 1 on the drug delivery device 100, to disengage the first part 10 from the second part 20, the user can deform the anchoring hooks 30 and free the abutment 31. Once the first part 10 and the second part 20 are disassembled, the user is then able to assemble the adaptor 1 in two successive steps, a first step during which he assembles and fixes the first part 10 on the distal tip 102 of the drug delivery device 100 and a second step during which he secures the second part 20 on the first part 10 as already described above.

After the fixing at least the first part 10 of the adaptor 1 with the drug delivery device 100, as shown on FIG. 2, the proximal access 33 to the anchoring hooks 30 is no more accessible by the user. Therefore, the second part 20 cannot be disassembled from the first part 10. The first part 10 is securely attached to the distal tip 102 by unreleasable fixing means, and therefore the second part 20 is securely attached to the drug delivery device 100 by the securing means (30, 31) and positioning means (41, 42).

In another embodiment, the preassembled first and second part 10, 20 are assembled on the distal tip 102 anchored to each other. In this case, the first part 10 can be fixed to the distal tip 102 for example by gluing or by using any other suitable means.

In another embodiment not shown, at least one of the first or second parts is provided with a specific access to enable the disengagement of the securing means even though the adaptor is assembled onto a drug delivery device.

The adaptor 1 of the invention therefore allows connecting reliably and safely a drug delivery device 100 to a connector without having to fear the adaptor 1 may detach from the drug delivery device 100. In addition, by providing a two parts adaptor, this allow to wash and siliconize the drug delivery device 100 fitted with the first part 10 without any effect on the material the second part 20 is made of. Therefore, there is a wider range of material that can be used for the second part 20.

The invention claimed is:

1. An adaptor for a drug delivery device comprising at least a container for a product, said container comprising a distal tip and an axial passageway defined through said distal tip, said adaptor having a longitudinal axis and being intended to be mounted on said distal tip, said adaptor including a first part and a second part, said first part having a first end and a second end and defining an engagement hole therethrough for receiving said distal tip of said container, said engagement hole defining an attachment able to attach said first part to an outer surface of said distal tip, said second part being provided with a connector able to connect said second part to a second connector, said adaptor further including a securer for securing said first part to said second part, wherein said first part comprises at least one anchoring hole spaced entirely radially away from the longitudinal axis of the adaptor, and wherein said securer extends into and is engaged with said at least one anchoring hole to secure said first part to said second part.

2. The adaptor according to claim 1, wherein said first part has an annular shape and is sized and shaped to receive said distal tip, said attachment including at least one attaching surface located on an inner surface of said first part.

3. The adaptor according to claim 2, wherein the at least one attaching surface comprises a rough surface.

4. The adaptor according to claim 1, wherein said at least one anchoring hole comprises a plurality of anchoring holes, wherein said first part is provided with a plurality of anchoring abutments, said second part being provided with a plurality of anchoring hooks, one of said anchoring abutments and said anchoring hooks being elastically deformable to allow their engagement respectively with the other one of said anchoring abutments and said anchoring hooks, said anchoring abutments and said anchoring hooks being arranged to prevent, when engaged with each other, a longitudinal displacement of said first part and said second part apart from each other, said anchoring abutments and said anchoring hooks forming at least part of said securer, wherein the anchoring hooks are configured to respectively engage the anchoring abutments in the anchoring holes.

5. The adaptor according to claim 4, further comprising an access area able to allow access to said elastically deformable anchoring abutments or anchoring hooks by a user when said first part and said second part are secured to each other, in order to elastically deform said elastically deformable anchoring abutments or anchoring hooks and release said securer.

6. The adaptor according to claim 1, wherein said first part and said second part are separate from each other.

7. The adaptor according to claim 1, wherein said first part and said second part are secured to each other.

8. The adaptor according to claim 1, further comprising a positioner provided partly on said first part and partly on said second part and able to prevent, when said first part and said second part are secured to each other, an angular displacement of said first part in regards to said second part.

9. The adaptor according to claim 8, wherein one of said first part and said second part is provided with at least one positioning peg, the other one of said first part and said second part being provided with at least one positioning hole arranged to receive said at least one positioning peg when said first part and said second part are secured to each other, said at least one positioning hole and said at least one positioning peg forming at least part of said positioner.

10. The adaptor according to claim 1, wherein said second part is provided with at least one thread forming at least partially said connector.

11. The adaptor according to claim 1, wherein said second part is provided with a closure intended to close a distal end of said second part, said closure being engaged with said connector.

12. The adaptor according to claim 1, wherein said second part has an annular shape with at least one traversing engagement hole defined therethrough along said longitudinal axis.

13. The adaptor according to claim 1, wherein said first part and said second part are made of different materials.

14. The adaptor according to claim 1, wherein said first part comprises at least one of polycarbonate, polyoxymethylen (POM) and combinations thereof.

15. The adaptor according to claim 1, wherein said second part comprises at least one of polystyrene shock, polypropylene and combinations thereof.

16. A drug delivery device comprising at least the container for the product and the adaptor according to claim 1, said container comprising the distal tip and the axial passageway defined through said distal tip.

17. The drug delivery device according to claim 16, wherein at least said first part of said adaptor is mounted on said distal tip, said first part being fixed to said distal tip by an unreleasable fixer.

18. The drug delivery device according to claim 17, wherein said unreleasable fixer comprises at least one of gluing, fretting, binding, melting and combinations thereof.

19. The drug delivery device according to claim 16, wherein said second part of said adaptor is secured to said first part, said securer securing said first part to said second part.

20. The drug delivery device according to claim 16, wherein said container comprises glass.

21. A method for mounting the adaptor according to claim 1 onto the drug delivery device comprising at least the container for the product, said container comprising the distal tip and the axial passageway defined through said distal tip, said method comprising at least the following steps:

providing the adaptor comprising the first part and the second part separate from each other, mounting said first part of said adaptor on the outer surface of said distal tip by fixing said first part to said distal tip with an unreleasable fixer, engaging said second part of said adaptor with said first part and anchoring said second part to said first part by said securer.

22. The method according to claim 21, wherein said adaptor being provided in the first place with the first part and the second part secured to each other by said securer, wherein said securer is disengaged in order to detach said first part and said second part from each other, so as to provide said adaptor with the first part and the second part separate from each other.

23. The method according to claim 21, wherein said unreleasable fixer comprises at least one of gluing, fretting, binding, melting and combinations thereof.

24. The adaptor according to claim 1, wherein the at least one anchoring hole is spaced entirely radially away from the engagement hole.

* * * * *